(12) United States Patent
Benetti et al.

(10) Patent No.: US 7,901,697 B2
(45) Date of Patent: Mar. 8, 2011

(54) SYNTHETIC THICKENERS FOR COSMETICS

(75) Inventors: Arianna Benetti, Gallarate (IT); Gianmarco Polotti, Sesto San Giovanni (IT); Franco Federici, Busto Araizio (IT); Guiseppe Li Bassi, Gavirate (IT)

(73) Assignee: Lamberti SpA, Albizzate (IT)

( * ) Notice: Subject to any disclaimer, the term of this patent is extended or adjusted under 35 U.S.C. 154(b) by 1471 days.

(21) Appl. No.: 10/560,416

(22) PCT Filed: Jun. 24, 2003

(86) PCT No.: PCT/IT03/00389
§ 371 (c)(1),
(2), (4) Date: Dec. 13, 2005

(87) PCT Pub. No.: WO2004/113393
PCT Pub. Date: Dec. 29, 2004

(65) Prior Publication Data
US 2006/0147404 A1 Jul. 6, 2006

(51) Int. Cl.
*A61K 8/02* (2006.01)
*A61K 9/00* (2006.01)
(52) U.S. Cl. .......................... 424/401; 424/400
(58) Field of Classification Search .................. None
See application file for complete search history.

(56) References Cited

U.S. PATENT DOCUMENTS 5,169,540 A * 12/1992 Fillipo et al. ............... 210/728
5,721,313 A * 2/1998 Yeung et al. ............... 524/814
6,197,287 B1 3/2001 Mallo et al.
6,329,483 B1 12/2001 Schade et al.
6,375,959 B1 4/2002 Mallo et al.
2001/0023284 A1 9/2001 Candau et al.

FOREIGN PATENT DOCUMENTS

EP 0 503 853 A2 9/1992
EP 1 059 305 A1 12/2000

* cited by examiner

*Primary Examiner* — Robert A Wax
*Assistant Examiner* — Melissa S Mercier
(74) *Attorney, Agent, or Firm* — Mossman, Kumar & Tyler, PC

(57) ABSTRACT

Disclosed are inverse emulsions for the preparation of cosmetic formulations wherein the weight ratio between the aqueous phase and the organic phase is from 4:1 and 2:1 and containing Ron 20 to 70% buy weight of an acrylic polymer obtained by inverse emulsion polymerisation of from 55 to 75% by weight of an anionic acrylic monomer containing a strongly acidic functional group; Ron 0.1 to 5% by weight of a cationic acrylic monomer if the formula (I). Wherein $R_1$ is hydrogen or methyl; $R_2$, $R_3$, $R_4$ are, one independently of the others, hydrogen or $C_1$-$C_4$ alkyl; Y is NH or O; A is a $C_1$-$C_6$ alkylene; from 25 to 45% by weight of a $C_3$-$C_5$ anionic acrylic monomer containing a carboxylic group. Also disclosed is the procedure for their preparation.

6 Claims, No Drawings

SYNTHETIC THICKENERS FOR COSMETICS

The present invention relates to inverse emulsions useful as thickener in cosmetic formulations and to the procedure for their preparation.

Particularly the inverse emulsions of the invention comprise a polymer obtained by polymerisation of two or more acrylic anionic monomers, at least one of which containing a strong acid functionality (and more specifically a sulfonic functional group), and of at least one monomer containing cationic groups.

The inverse emulsions of the invention possess high skin and hair compatibility, which makes them particularly suited for the preparation of cosmetic formulations, and exhibit good thickening properties and stability over time.

With the expression "cosmetic formulations" we mean the products normally used for personal care, such as body and face creams, hair gels and lotions, hair colouring and bleaching creams, sunscreen compositions, make-up products, cleansing, moisturizing and perspiring fluids and other products for similar applications.

It is known that a technical problem often encountered in the cosmetic industry is to obtain high viscous formulations (pastes, gels) stable over time and exhibiting high compatibility with skin and hair.

An essential characteristic of the thickeners employed in cosmetic formulations is that they manifest their thickening capability without negatively altering the other properties of the formulations.

In the specialised literature many methods are reported to regulate the rheological properties of different formulations, often including the use of polymers in the form of inverse emulsion (an inverse emulsion is an emulsion containing both an oil-in-water emulsifier and a water-in-oil emulsifier, wherein the aqueous phase is dispersed in the organic phase in very small drops), but the synthetic thickeners for cosmetics of the present invention are never described.

We cite as an example:
- EP 503853, wherein an inverse emulsion containing a polymer comprising units deriving from acrylamide, 2-acrylamido-2-methylpropanesulfonic acid and a polyfunctional monomer is described; a disadvantage of the inverse emulsions of EP 503853 is the fact that they contain traces of acrylamide, a toxic substance which is unacceptable by the present European legislative trend;
- U.S. Pat. No. 6,375,959 and U.S. Pat. No. 6,197,287 wherein a procedure for the preparation of cross-linked or branched polyelectrolytes based on strongly acidic monomers and other monomers, but not acrylamide, in the form of an inverse emulsion, is described;
- U.S. Pat. No. 6,329,483, wherein copolymers of carboxylic acids and quaternary ammonium compounds and the preparation of gels and emulsions containing the same is described;
- US 2001/0023284, wherein copolymers of a neutral monomer (N-alkylacrylamide) with one or more monomers selected among cationic monomers, monomers bearing strongly acidic functional groups and monomers bearing weakly acidic functional groups are described.

It is still desirable in the cosmetic field to have thickeners in the form of stable emulsion that are able to give stable cosmetic formulations, and that, in addition to a good thickening efficiency in different conditions and ease of use, exhibit an improved compatibility with skin and hairs. With the expression "stable emulsion" we mean an emulsion that in the normal storing conditions (from −10° C. to 40° C.) and for the usual lifetime (180-360 days) does not show phase separation, sediment, formation of floating pellicles and lumps.

With the expression "stable cosmetic product" we mean a cosmetic formulation that in the above said conditions and lifetime does not show phase separation, sediment, formation of floating pellicles and lumps.

By cosmetic product with high compatibility with skin and hair we mean a product that is easily absorbed through a keratinous substrate while making changes in the touch, in moisturisation and perspiration, and improving the general sensorial characteristics without altering the physiological pH.

It has now surprisingly been found that the inverse emulsions containing an acrylic polymer obtained by inverse emulsion polymerisation of an anionic acrylic monomer containing a weakly acidic functional group, an anionic acrylic monomer containing a strongly acidic functional group and an acrylic cationic monomer of the formula (I)

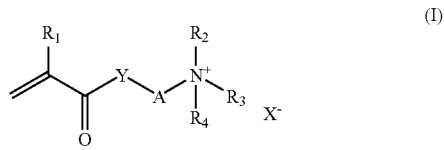

wherein
$R_1$ is hydrogen or methyl;
$R_2$, $R_3$, $R_4$ are, one independently of the others, hydrogen or $C_1$-$C_4$ alkyl;
Y is NH or O;
A is a $C_1$-$C_6$ alkylene; X is chloride,
possess a stability which is perfectly suited for their industrial use in cosmetic formulations, even many months after their preparation; furthermore the inverse emulsions of the invention enable the preparation of cosmetic formulations with very good compatibility with skin and hair. It is well known that the combined presence of two different functionalities in the same macromolecule, a cationic one and an anionic one, tends to be the cause of coagulation; coagulation can occur both in the phase preceding the reaction (when monomers having opposed functionality are mixed together), and while the reaction takes place, during the polymer formation.

An insufficient distribution of the charges in the macromolecule itself increases its solubility in the oily phase and leads to its desorption from the water phase where the reaction takes place.

The polymer desorption and its consequent dissolution in the oily phase usually causes the coagulation of the dispersed system and gelation.

It has surprisingly been observed that coagulation and gelation can be prevented by operating within the limits of the present invention.

It is a fundamental object of the present invention an inverse emulsion for the preparation of cosmetic formulations wherein the weight ratio between the aqueous phase and the organic phase is from 4:1 to 2:1 and containing from 20 to 70% by weight of an acrylic polymer obtained by inverse emulsion polymerisation of
i. from 55 to 75% by weight, and preferably from 60 to 70% by weight, of an anionic acrylic monomer containing a strongly acidic functional group;
ii. from 0.1 to 5% by weight, and preferably from 2 to 4% by weight, of a cationic acrylic monomer of the formula (I)

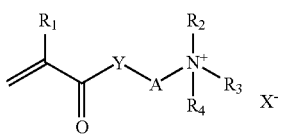

wherein
$R_1$ is hydrogen or methyl;
$R_2$, $R_3$, $R_4$ are, one independently of the others, hydrogen or $C_1$-$C_4$ alkyl;
Y is NH or O;
A is a $C_1$-$C_6$ alkylene; X is chloride,
iii. from 25 to 46% by weight, and preferably from 30 to 40% by weight, of a $C_3$-$C_5$ anionic acrylic monomer containing a carboxylic group.

The anionic acrylic monomer containing a strongly acidic functional group is selected among the monomer of this kind that are normally employed for the preparation of polymeric synthetic thickeners for the cosmetic use; among those, 2-acrylamido-2-methylpropanesulfonic acid is particularly suited for the realisation of the present invention.

Preferably the cationic acrylic monomer of the formula (I) is selected from acryloyloxyethyl-trimethylammonium chloride and methacryloyloxyethyl-trimethylammonium chloride and the $C_3$-$C_5$ anionic acrylic monomer containing a carboxylic group is selected from acrylic acid and methacrylic acid.

According to a fundamental aspect of the invention the acrylic polymer obtained by inverse emulsion polymerisation is cross-linked with from 0.01 to % by weight of a compound containing two or more ethylenic groups, preferably with methylene-bis-acrylamide.

It is a further object of the present invention a procedure for the preparation of an inverse emulsion for cosmetic formulations characterised by:

a. preparing a composition consisting of from 40 to 60% by weight of water, and for the remaining percentage by weight of a mixture of acrylic monomers consisting of:
i. from 55 to 75% by weight, and preferably from 60 to 70% by weight, of an anionic acrylic monomer containing a strongly acidic functional group;
ii. from 0.1 to 5% by weight, and preferably from 2 to 4% by weight, of a cationic acrylic monomer of the formula (I)

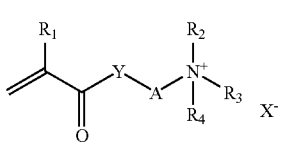

wherein
$R_1$ is hydrogen or methyl;
$R_2$, $R_3$, $R_4$ are, one independently of the others, hydrogen or $C_1$-$C_4$ alkyl;
Y is NH or O;
A is a $C_1$-$C_8$ alkylene; X is chloride,
iii. from 25 to 45% by weight, and preferably from 30 to 40% by weight, of a $C_3$-$C_5$ anionic acrylic monomer containing a carboxylic group;
b. adding to the composition prepared in a. an aqueous solution of an alkali to regulate the pH between 4 and 7, a cross-linking agent and an initiator of radical polymerisation, maintaining the temperature between 3 and 7° C.;
c. preparing an organic phase containing one or more water-in-oil emulsifiers;
d. introducing the mixture obtained in be into the organic phase prepared in c. and emulsifying the two phases by vigorous stirring;
e. initiating the polymerisation and completing it maintaining the temperature between 55 and 95° C. under vigorous stirring;
f. cooling the reaction mixture to 35-45° C. and adding an oil-in-water emulsifier.

As it was previously said about the inverse emulsion of the invention, the anionic acrylic monomer containing a strongly acidic functional group is selected among the monomers that are normally employed for the preparation of polymeric synthetic thickeners for the cosmetic use; among those, 2-acrylamido-2-methylpropanesulfonic acid is particularly suited for the realization of the present invention.

Preferably the cationic acrylic monomer of the formula (I) is selected from acryloyloxyethyl-trimethylammonium chloride and methacryloyloxyethyl-trimethylammonium chloride and the $C_3$-$C_5$ anionic acrylic monomer containing a carboxylic group is selected from acrylic acid and methacrylic acid.

In the procedure of the invention, normally, the alkali used is NaOH.

According to another aspect of the invention, the acrylic polymer obtained by inverse emulsion polymerisation is cross-linked with from 0.01 to 1% by weight of a compound containing two or more ethylenic groups, preferably with methylene-bis-acrylamide.

Among the initiators of radical polymerisation utilisable for the realisation of the present invention are ammonium, potassium or sodium persulfate, and water-soluble organic peroxides, by way of example hydrogen peroxide and peracetic acid.

In the inverse emulsions of the invention the organic phase consists of by mineral oils containing saturated hydrocarbons or by vegetable oils or by mixture thereof having boiling point from 150 to 300° C.

Preferably the organic phase is a $C_{13}$-$C_{16}$ iso-paraffin.

The water-in-oil and the oil-in-water emulsifiers are those normally used for this purpose.

We cite among the utilisable water-in-oil emulsifiers: sorbitan monolaurate, sorbitan monopalmitate, sorbitan monostearate, sorbitan monooleate; among the utilisable oil-in-water emulsifiers we cite the linear or branched ethoxylated alcohols.

To initiate the polymerisation of the acrylic monomers advantageously an aqueous solution of sodium metabisulfite is used.

The inverse emulsions of the invention may further additionally contain the common additives used in radical polymerisation, by way of example sequestering agents such as sodium diethylenetriaminepentaacetate.

As it was previously observed, the inverse emulsions of the present invention are particularly suited for the treatment of hair and skin, in body and face creams, hair gels and lotions, hair colouring and bleaching creams, sunscreen compositions, make-up products, cleansing, moisturizing and perspiring fluids.

In the following examples the preparation of inverse emulsions according to the invention and of some cosmetic formulations containing them is reported.

The following examples illustrate the present invention without limiting it, nor the kind of application of the inverse emulsions of the invention.

EXAMPLE 1

The following ingredients are loaded into a 1.5 l pirex reactor equipped with a steel anchor stirrer:
62.21 g deionised water;
573 g aqueous solution (50% by weight) of sodium 2-acrylamido-2-methylpropane sulfonate;
135 g acrylic acid;
15.8 g ADAMQUAT MC 80 (acryloyloxyethyl-trimethyl ammonium chloride sold by Atofina).

After a cooling down period, necessary to reach a temperature close to 0° C., the following ingredient are slowly added while stirring:
112.38 g aqueous solution (50% by weight) of NaOH;
10 g aqueous solution (1% by weight) of methylene-bisacrylamide;
0.5 g aqueous solution (40% by weight) of sodium diethylenetriaminepentaacetate;
10.75 g aqueous solution (4% by weight) of ammonium persulfate.

In the meantime, the organic phase is prepared inside a 500 ml beaker adding under stirring:
20 g sorbitan monooleate;
214.8 g $C_{13}$-$C_{16}$ hydrocarbon isoparaffin.

The aqueous phase is slowly added into the organic phase and subsequently the mixture is efficiently stirred with a high shear dispersing machine (ultra-turrax IKA).

The emulsion obtained is then reloaded in the reactor and the reaction is ready to be started (reaction phase). The first operation is to insufflate nitrogen directly in the bulk of the product for about 10 minutes. This is a key step, because it enables to lower and control the amount of oxygen dissolved in the emulsion and to adjust the induction times. The second phase takes place only after the emulsion temperature is warmed up to 20° C. After that, 21.5 g of a 1% by weight aqueous solution of sodium metabisulfite is quickly loaded drop-wise through an addition funnel. The third phase is the radical reaction. The reaction proceeds spontaneously raising gradually the temperature to about 60° C. in 50 minutes. The stirring is maintained very fast and cool water re-circulates inside the reactor jacket. After this period of time the emulsion is kept at 60° C. for about one hour to complete the monomers conversion, consuming the residual monomers. Subsequently a cooling down period is required to reach a temperature of 35-40° C. The final step is the addition of 25 g of $C_{12}$-$C_{16}$ (8 moles) ethoxylated linear alcohol.

The mixture is rapidly stirred till homogeneity is reached; the final emulsion (Emulsion 1) is then unloaded and stored for at least 24 hours before the evaluation of its properties.
Property Evaluation of Emulsion 1.

Samples of Emulsion 1 are stored at different temperatures.

The emulsion stability is evaluated at different temperatures by visually checking possible phase separation or settling on the bottom of the vessel using a glass stick.

In the following table (Table 1) the test temperatures and minimal stability times of the emulsion are shown.

TABLE 1

|  | Temperature | | |
| --- | --- | --- | --- |
|  | −3° C. | 20° C. | 45° C. |
| Stability (days) | >30 | >100 | >30 |

The thickening properties are instead evaluated as follows and are shown in Tables 2 and 3.

A 2% by weight aqueous solution of Emulsion 1 is prepared in deionized water with high stirring in a 1 litre beaker. Subsequently the viscosity is measured at 20° C., at different pH values (see Table 2) and adding different concentration of electrolyte (NaCl, as shown in Table 3).

The pH was adjusted by additions of an aqueous solution (50%) of citric acid.

TABLE 2

Brookfield Viscosity in mPa · s (spindle 6, after 24 h)

| 5 rpm | 10 rpm | pH |
| --- | --- | --- |
| 70000 | 41000 | 6.8 |
| 13200 | 8200 | 6.6 |
| 3200 | 2100 | 5.2 |
| 400 | 300 | 4.2 | rpm = rounds per minute

TABLE 3

Brookfield Viscosity in mPa · s (spindle 6, after 24 h, pH = 7.5)

|  | 0% NaCl | 0.01% NaCl | 0.02% NaCl | 0.03% NaCl | 0.04% NaCl |
| --- | --- | --- | --- | --- | --- |
| 5 rpm | 70000 | 52200 | 38000 | 26400 | 18800 |
| 10 rpm | 41000 | 30000 | 22000 | 16000 | 11500 | rpm = rounds per minute

EXAMPLE 2

An inverse emulsion is prepared as described in Example 1, substituting ADAMQUAT MC 80 in the aqueous phase with 16.9 g of MADQUAT MC 75 (methacryloyloxyethyl-trimethyl ammonium chloride, 75% by weight in water, sold by Atofina) thus obtaining Emulsion 2.
Property Evaluation of Emulsion 2.

Samples of Emulsion 2 are stored at different temperatures.

The emulsion stability is evaluated at different temperatures by visually checking possible phase separation or settling on the bottom of the vessel using a glass stick.

In the following table (Table 4) the test temperatures and minimal stability times of the emulsion are shown.

TABLE 4

|  | Temperature | | |
| --- | --- | --- | --- |
|  | −3° C. | 20° C. | 45° C. |
| Stability (days) | >30 | >100 | >30 |

The thickening properties are evaluated as described for Emulsion 1 and are shown in Tables 5 and 6.

TABLE 5

Brookfield Viscosity in mPa · s (spindle 6, after 24 h)

| 5 rpm | 10 rpm | pH |
| --- | --- | --- |
| 77000 | 45600 | 7.1 |
| 61800 | 36600 | 6.9 |
| 30000 | 17500 | 6.4 |
| 17800 | 10700 | 6.1 |
| 7000 | 4500 | 5.6 |
| 800 | 600 | 4.7 | rpm = rounds per minute

TABLE 6

Brookfield Viscosity in mPa·s (spindle 6, after 24 h, pH = 7.5)

|  | 0% NaCl | 0.01% NaCl | 0.02% NaCl | 0.03% NaCl | 0.04% NaCl |
|---|---|---|---|---|---|
| 5 rpm | 77000 | 64000 | 49600 | 39000 | 27800 |
| 10 rpm | 45600 | 38000 | 29400 | 23100 | 16200 | rpm = rounds per minute

EXAMPLE 3

A body cream is prepared using Emulsion 1; all the ingredients are listed in Table 7 and the procedure is described in the following paragraph.

TABLE 7

Body cream.

| Ingredients | % |
|---|---|
| Phase A | |
| Aqua | to 100 |
| Glycerin | 3 |
| EDTA | 0.1 |
| Emulsion 1 | 0.4 |
| Phase B | |
| Hydrogenated Polydecene | 15 |
| *Prunus Amygdalus dulcis* | 5 |
| Caprylic/capric triglyceride | 4 |
| Steareth-2 | 2 |
| Steareth-21 | 3 |
| Phase C | |
| Preservative | 1 |
| Phase D | |
| Parfum | 0.1 |

Phase A is prepared by homogenising all the ingredients at room temperature and then heating the mixture to 70° C.

Phase B is prepared heating all the ingredients to 70-75° C.; Phase A is added to Phase B stirring vigorously. The mixture is cooled down to 40° C. and Phase C and Phase D are added, stirring till homogeneity is reached.

Properties of the Cream Obtained:
Viscosity=31000 mPa·s (5 rpm, spindle 4); 44500 mPa·s (2.5 rpm spindle 4)
pH=7.3

EXAMPLE 4

A foundation is prepared using Emulsion 2; all the ingredients are listed in Table 8 and the procedure is described in the following paragraph.

TABLE 8

Foundation.

| Ingredients | % |
|---|---|
| Phase A | |
| Aqua | to 100 |
| Glycerin | 3 |
| EDTA | 0.1 |
| Emulsion 2 | 0.4 |

TABLE 8-continued

Foundation.

| Ingredients | % |
|---|---|
| Phase B | |
| Hydrogenated Polydecene | 15 |
| *Prunus Amygdalus dulcis* | 5 |
| Caprylic/capric triglyceride | 4 |
| Steareth-2 | 2 |
| Steareth-21 | 3 |
| Unipure Brown LC889* | 8 |
| Unipure Yellow LC182* | 1 |
| Unipure White LC 981* | 1 |
| Phase C | |
| Preservative | 1 |
| Phase D | |
| Parfum | 0.1 |

*pigments sold by LCW (France)

All the ingredients of Phase B are mixed and stirred till homogeneity is reached. Phase A is prepared by mixing all its ingredients and heating to 70° C.; then Phase A is added to Phase B. The mixture of the two phases is homogenised and then cooled down to 40° C.

Phase C and D are added while stirring.

Properties of the Foundation:
Viscosity=29500 mPa·s (5 rpm, spindle 4); 48000 mPa·s (2.5 rpm, spindle 4); pH=6.9.
Stability.

No separation after 60 minutes of centrifugation at 6000 rpm.

The invention claimed is:

1. A procedure for preparing a cosmetic comprising preparing the cosmetic using an inverse emulsion having an aqueous phase and an organic phase comprising from about 20 to about 70% by weight of an acrylic polymer obtained by inverse emulsion polymerization of
   i. from about 55 to 76% by weight of an anionic acrylic monomer containing a strongly acidic functional group wherein the anionic acrylic monomer containing a strongly acidic functional group is 2-acrylamido-2-methylpropanesulfonic acid;
   ii. from about 0.1 to 5% by weight of a cationic acrylic monomer of the formula (I):

$$\begin{array}{c}R_1\\ \diagup\\ \diagdown\end{array}\!\!-\!\!\overset{O}{\underset{\|}{C}}\!-\!Y\!-\!A\!-\!\overset{R_2}{\underset{R_4}{\overset{|}{N^+}\!-\!R_3}}\quad X^- \qquad (I)$$

wherein $R_1$ is hydrogen or methyl;
   $R_2$, $R_3$, $R_4$ are, one independently of the others, hydrogen or a C1-C4 alkyl;
   Y is NH or O;
   A is a $C_1$-$C_6$ alkylene; and
   X is chloride; and
   iii. from about 25 to 45% by weight of a $C_3$-$C_5$ anionic acrylic monomer containing a carboxylic group;
   wherein the weight ratio between the aqueous phase and the organic phase is from about 4:1 to about 2:1.

2. The procedure according to claim 1, wherein the acrylic polymer is obtained by the inverse emulsion polymerization of:

i. from about 60 to 70% by weight of an anionic acrylic monomer containing a strongly acidic functional group wherein the anionic acrylic monomer containing a strongly acidic functional group is 2-acrylamido-2-methylpropanesulfonic acid;
ii. from about 2 to 4% by weight of a cationic acrylic monomer of the formula (I); and
iii. from about 30 to 40% by weight of a $C_3$-$C_5$ anionic acrylic monomer containing a carboxylic group.

3. The procedure according to claim 2, wherein the cationic acrylic monomer of the formula (I) is selected from the group consisting of acryloyloxylethyl triethylammonium chloride and methacryloyloxyethyl trimethylammonium chloride.

4. The procedure according to claim 2, wherein the $C_3$-$C_5$ anionic acrylic monomer containing a carboxylic group is selected from the group consisting of acrylic acid and methacrylic acid.

5. The procedure according to claim 1, wherein the acrylic polymer obtained by inverse emulsion polymerization is cross-linked with from about 0.01 to about 1% by weight of a compound containing two or more ethylenic groups.

6. The procedure according to claim 5, wherein the acrylic polymer obtained by inverse emulsion polymerization is cross-linked with methylene-bis-acrylamide.

* * * * *